(12) United States Patent
Dragicevic et al.

(10) Patent No.: US 12,198,068 B2
(45) Date of Patent: *Jan. 14, 2025

(54) EARPIECE ADVISOR

(71) Applicant: BRAGI GmbH, Munich (DE)

(72) Inventors: Darko Dragicevic, Munich (DE); Peter Vincent Boesen, Munich (DE)

(73) Assignee: BRAGI GMBH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/306,925

(22) Filed: Apr. 25, 2023

(65) Prior Publication Data

US 2023/0259793 A1     Aug. 17, 2023

Related U.S. Application Data

(63) Continuation of application No. 16/165,357, filed on Oct. 19, 2018, now Pat. No. 11,651,238.

(60) Provisional application No. 62/574,888, filed on Oct. 20, 2017.

(51) Int. Cl.
| | |
|---|---|
| *G06N 5/022* | (2023.01) |
| *G06Q 30/0601* | (2023.01) |
| *G16H 20/00* | (2018.01) |
| *H04R 1/10* | (2006.01) |
| *H04R 25/00* | (2006.01) |

(52) U.S. Cl.
CPC ......... *G06N 5/022* (2013.01); *G06Q 30/0631* (2013.01); *G16H 20/00* (2018.01); *H04R 1/1016* (2013.01); *H04R 25/75* (2013.01); *H04R 2225/41* (2013.01); *H04R 2225/55* (2013.01); *H04R 2420/07* (2013.01); *H04R 2460/07* (2013.01); *H04R 2499/11* (2013.01)

(58) Field of Classification Search
None
See application file for complete search history.

(56) References Cited

U.S. PATENT DOCUMENTS

| | | | |
|---|---|---|---|
| 11,651,238 B2 * | 5/2023 | Dragicevic | G06N 5/022 706/46 |
| 2013/0039517 A1 | 2/2013 | Nielsen | |
| 2014/0046230 A1 | 2/2014 | Winkler | |
| 2016/0124707 A1 | 5/2016 | Ermilov | |
| 2017/0188129 A1 | 6/2017 | Sindia | |
| 2018/0322861 A1 | 11/2018 | Ibrahim | |

* cited by examiner

*Primary Examiner* — Hemant S Patel
(74) *Attorney, Agent, or Firm* — Goodhue, Coleman & Owens, P.C.

(57) ABSTRACT

An earpiece in embodiments of the present invention may have one or more of the following features: (a) an earpiece housing, (b) at least one speaker, (c) a plurality of sensors disposed within the earpiece housing, and (d) a processor disposed within the earpiece housing and operatively connected to the plurality of sensors and the at least one speaker, wherein the processor is configured to use an artificial intelligence framework to evaluate sensor input from the plurality of sensors to provide advice to the user.

20 Claims, 5 Drawing Sheets

EARPIECE ADVISOR

PRIORITY STATEMENT

This application is a continuation of U.S. Non-provisional patent application Ser. No. 16/165,357, filed on Oct. 19, 2018 which claims priority to U.S. Provisional Patent Application No. 62/574,888, filed on Oct. 20, 2017, both titled Earpiece Advisor, all of which are hereby incorporated by reference in their entirety.

FIELD OF THE INVENTION

The present invention relates to wearable devices. Particularly, the present invention relates to providing helpful advice to a user through a wearable device. More particularly, but not exclusively, the present invention relates to ear pieces and other hearables, virtual assistants, smart hardware with sensing capabilities and artificial intelligence.

BACKGROUND

Advances in wireless communications have allowed for data sharing innovations. A user can use a mobile device (e.g., phones, tablet computers, watches, etc.) to open various applications/programs, and operate the various devices to communicate with other mobile devices. Development of the Internet of Things (IOT) reflects a growing trend to wirelessly connect to and control a variety of services.

Users can generally access a variety of services on their mobile devices. Technology platforms of various types are used to support marketing and advertising efforts. For example, broadcast television and radio include advertising. Search engines and social media platforms including advertising or sponsored content. This advertising and marketing may be important to the provider of the technology platform as a part of their monetization efforts. To some extent users may recognize they are benefitting from the advertising and marketing as they may receive services without paying a subscription and thus users may be willing to tolerate a limited amount of advertising.

However, too much advertising can be distractive to users and cause them to abandon a technology platform. This may be especially true with audio technology platforms. What is needed are new and improved ways to provide opportunities for contextual or potentially sponsored content in a manner helpful to users and viewed favorably by users.

SUMMARY

Therefore, it is a primary object, feature, or advantage of the present invention to improve over the state of the art.

An earpiece in embodiments of the present invention may have one or more of the following features: (a) an earpiece housing, (b) at least one speaker, (c) a plurality of sensors disposed within the earpiece housing, and (d) a processor disposed within the earpiece housing and operatively connected to the plurality of sensors and the at least one speaker, wherein the processor is configured to use an artificial intelligence framework to evaluate sensor input from the plurality of sensors to provide advice to the user. The processor may be further configured to use the artificial intelligence framework to determine a contextually relevant time to deliver the advice to the user. The processor may be further configured to control delivery of the advice to the user at the contextually relevant time.

A device in embodiments of the present invention may have one or more of the following features: (a) a housing, (b) at least one speaker, (c) a plurality of sensors disposed within the housing, (d) a processor disposed within the housing and operatively connected to the plurality of sensors and the at least one speaker, wherein the processor is configured to use an artificial intelligence framework to evaluate sensor input from the plurality of sensors to provide advice to the user, and (e) a transceiver operatively connected to the processor for operative communication with a network of one or more additional devices.

A method of providing advice using a device in embodiments of the present invention may comprise one or more of the following steps: (a) monitoring a plurality of sensors using the device, (b) using an artificial intelligence platform of the device to generate advice to a user of the device based on contextual understanding, (c) determining where the user is located, (d) determining the user's activity, (d) determining whether the user has made any requests and wherein the advice is based at least in part on context of where the user is, what the user is doing and any requests made by the user.

One or more of these and/or other objects, features, or advantages of the present invention will become apparent from the specification and following claims. No single embodiment need provide every object, feature, or advantage. Different embodiments may have different objects, features, or advantages. Therefore, the present invention is not to be limited to or by an objects, features, or advantages stated herein.

BRIEF DESCRIPTION OF THE DRAWINGS

Illustrated embodiments of the disclosure are described in detail below with reference to the attached drawing figures, which are incorporated by reference herein.

Figure 1:
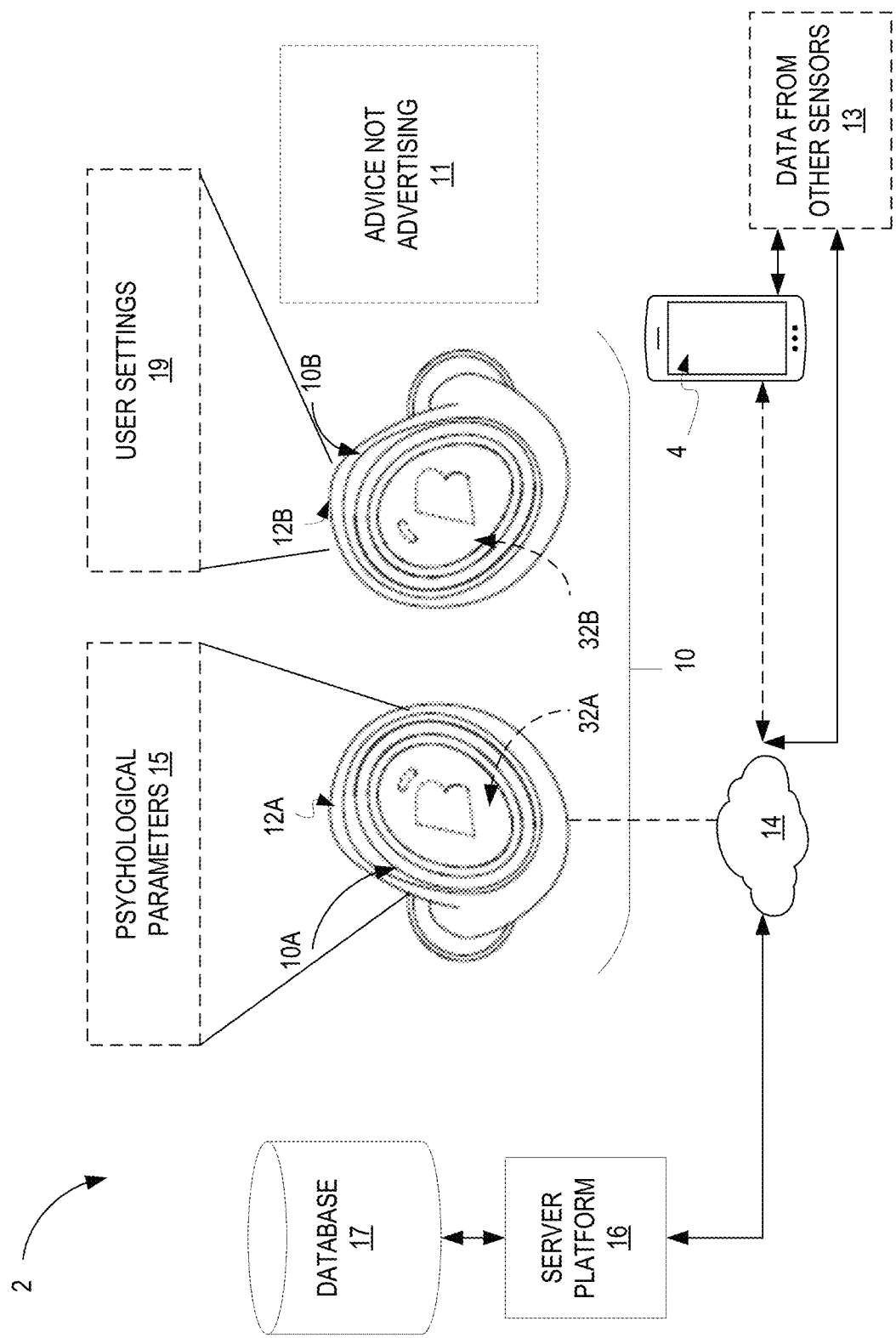
FIG. 1 illustrates one view of a set of wireless earpieces which provide advice as opposed to advertising in accordance with an embodiment of the present invention.

Some of the figures include graphical and ornamental elements. It is to be understood the illustrative embodiments contemplate all permutations and combinations of the various graphical elements set forth in the figures thereof.

DETAILED DESCRIPTION

The following discussion is presented to enable a person skilled in the art to make and use the present teachings. Various modifications to the illustrated embodiments will be clear to those skilled in the art, and the generic principles herein may be applied to other embodiments and applications without departing from the present teachings. Thus, the present teachings are not intended to be limited to embodiments shown but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings. While embodiments of the present invention are discussed in terms of wireless earpieces, it is fully contemplated embodiments of the present invention may be used in most any wearable device without departing from the spirit of the invention.

It is an object, feature, or advantage of the present invention to provide an audio technology platform which allows for providing an advisor which can suggest products, information or services to a user in a manner viewed as advice and recommendations.

It is a still further object, feature, or advantage of the present invention to provide an audio technology platform which allows for contextual or potentially sponsored content but in a manner not viewed as advertising.

Another object, feature, or advantage is to provide contextually aware useful recommendations, information, or advice to users.

Yet another object, feature, or advantage is to determine a contextually relevant time to delivery the advice to the user and to deliver the advice at the contextually relevant time.

According to one aspect, an earpiece includes an earpiece housing, at least one speaker, a plurality of sensors disposed within the earpiece housing, and a processor disposed within the earpiece housing and operatively connected to the plurality of sensors and the at least one speaker. The processor is configured to use an artificial intelligence platform to evaluate sensor input from the plurality of sensors to provide advice to the user. The processor may be further configured to use the artificial intelligence framework to determine a contextually relevant time to deliver the advice to the user. The processor may be further configured to control delivery of the advice to the user at the contextually relevant time. Sensors from connected devices may also be used to provide sensor input. The advice may be in a form of a product or service recommendation.

The present invention relates to ear pieces, ear phones, or other hearable or related devices, especially those which include virtual assistants and/or artificial intelligence. For example, wireless earpieces may present, recommend, or suggest products, information, or services. The present invention relates to using such devices to serve as advisors to users in a manner suggesting appropriate products or services at appropriate times. These suggestions may be made even if not specifically requested by a user, and in an unobtrusive manner to assist the user. Thus, the primary purpose is to assist the user with a secondary purpose of promoting products or services or providing contextual or potentially sponsored content.

For purposes of explanation a set of wireless earpieces is used. Although wireless earpieces are shown and described throughout it is to be understood other types of hearable or other wearable devices may be used instead. For example, instead of a set of wireless earpieces, a set of over-the ear earphones may be used. In addition, to hearable devices, other types of speaker-driven devices may be used which may take on any number of different form factors and need not be worn by a user.

The wireless earpieces provide multiple different sensors. The sensors may measure user biometrics, environmental information, location, activities/actions, nearby users, and so forth. These may include air microphones, bone microphones, inertial sensors, infrared/optical sensors, biometric sensors, and other types of sensors. All or a portion of this sensor information can be stored onboard the wireless earpiece in a memory.

Sensor information from external devices, systems, or components may also be made available for utilization as well. The wireless earpieces may be contextually aware so suggestions to a user may be made based on context. The context may include where the user is, what the user is doing, who the user is with, electronic devices being used by the user, biometric conditions of a user, or other context. The context may further include what the user is saying. Further, the sensor information may be used by AI (artificial intelligence) frameworks to better assess the context of a user's activities, prior experiences, known likes and dislikes, environment and surroundings to provide useful advice and recommendations helpful to a user.

FIG. 1 illustrates one example of a system 2. A set of wireless earpieces 10 is shown which includes both a left wireless earpiece 10A and a right wireless earpiece 10B. The left wireless earpiece 10A has a left earpiece housing 12A. The right wireless earpiece 10B has a right earpiece housing 12B. The set of wireless earpieces may include one or more sensors such as sensors 32A and 32B. The set of wireless earpieces may communicate over a network 14 with a server platform 16 and database 17. The server platform 16 may include any number of different hardware and software components including physical machines, operating systems, software applications, and/or other components. The server platform 16 may include or otherwise be in operative communication with a database 17. Instead of the set of wireless earpieces 10 communicating directly over the network 14, the set of wireless earpieces 10 may communicate through an intermediary device such as a mobile device 4. Thus, for example, the set of wireless earpieces 10 may communicate via Bluetooth or BLE with the mobile device 4 which may communicate over the network 14 using Wi-Fi or cellular communications with the server platform 16. Alternatively, the set of wireless earpieces 10 may communicate with the network 14 using Wi-Fi, cellular communications, Bluetooth, or other communications technologies.

The sensors 32A, 32B of the set of wireless earpieces 10 may be used to sense environment parameters and physiological/biometric parameters 15. In addition, user settings 19 may be stored in a memory 40 (see FIG. 2) of the wireless earpieces 10. The user settings 19 may include user specific information, data, preferences, historical selections, parameters, criteria, thresholds, historical data on selections and so forth. The user settings 19 may include personal preferences of multiple users as well as other user profile information created based on the user's activity. The biometric parameters 15 and the user settings 19 may be used to generate advice. This advice may evolve on-the-fly in response to changes in the environment parameters, biometric parameters and the user settings. Artificial intelligence framework 18 (FIG. 2) may use information from both user settings 19 and biometric/physiological parameters 15 to generate advice for user 106 (FIG. 3) based upon several conditions or environmental conditions of the user 106.

The sensors 32A, 32B help provide context. Any number of types of context may be provided including, is it warm or cold (such as measured using a temperature sensor), what is the time of day, what is a location, what is a user doing, who is around the user, what is the mood of the user, is the user stressed or relaxed, what is the user's heart rate, does the user need to focus or need a distraction, and other contextual information. Thus, the sensors 32A, 32B provide context. The sensors 32A, 32B may also be used to provide the user interface and user experience. For example, inertial sensors may be used to detect head movement and head orientation which is used to select menu items based on spatial context. The sensors 32A, 32B may be used to distinguish between Idle, Walking, Running, Cycling, Swimming, Sleeping, or other activities in addition to measuring heart rate, steps, pace, acceleration, G-force, direction, and other types of physiological data, body vitals, and performance data. These physiological parameters 15 can be stored in a memory onboard the wireless earpieces 10.

In addition to using the sensors 32A, other sensors may be used to collect data. This may be data 13 collected from sensors associated with other devices which are on a body area network or an IOT (Internet of Things) network (FIG. 3) or a combination of networks.

In operation, portions of processing may be provided at the server platform 16. For example, the database 17 may include information regarding different products or services and parameters or descriptors associated with the products or services. The server platform 16 may query the database 17 based on a request from the wireless earpieces 10 for products or services which meet parameters. This process may be performed in real-time or may be performed as a part of a batch process at a convenient time.

In one embodiment, the wireless earpieces 10 may include specific data sets or modules utilized to provide information or advice 11. The different modules may vary based on activity, location, situation (e.g., game, emergency, vacation, etc.), proximate users, and so forth. In another embodiment, the data sets may be retrieved from the server platform 16 or the database 17 for utilization by the wireless earpieces 10 or the mobile device 4.

Figure 2:
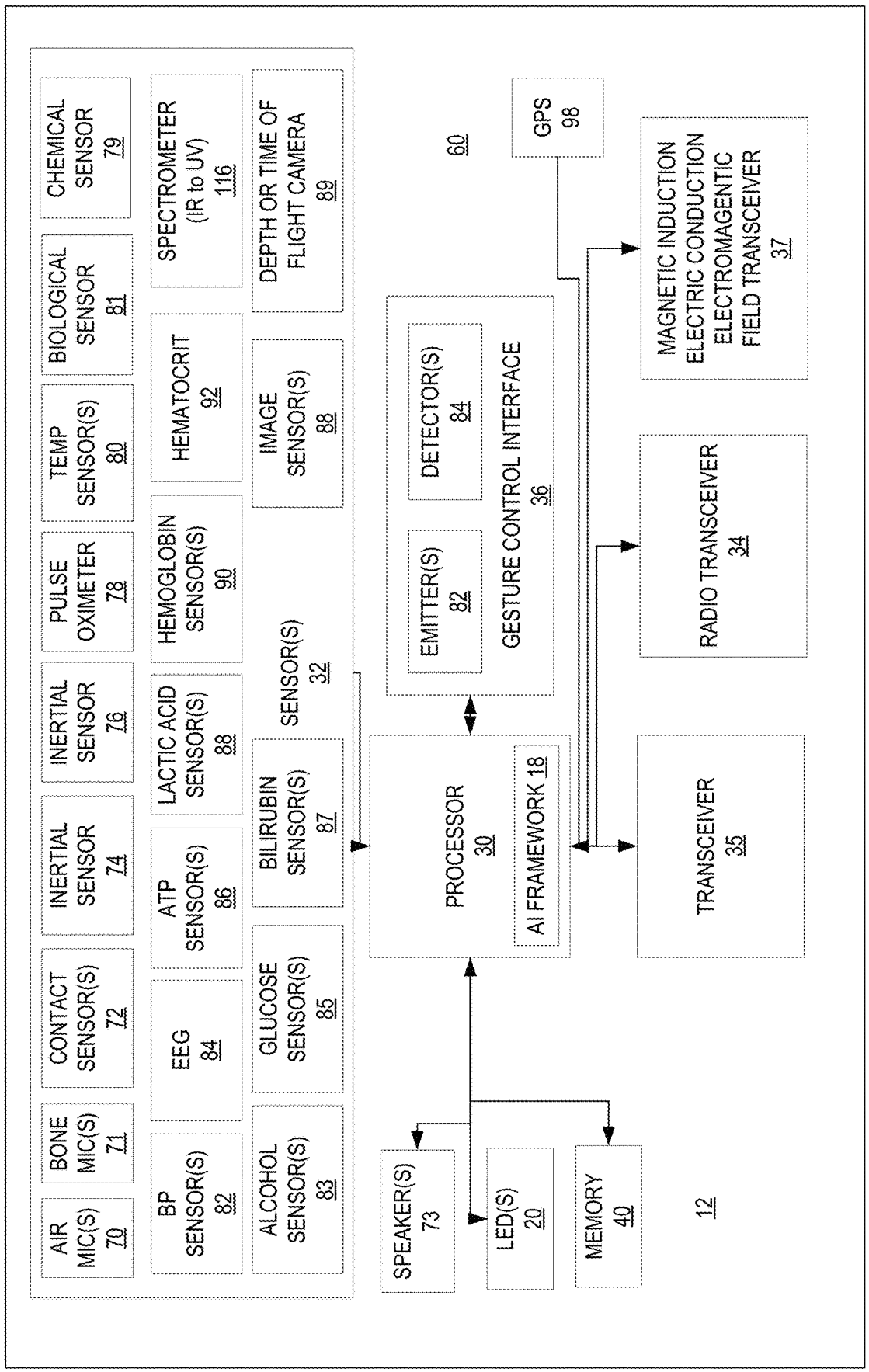
FIG. 2 is a block diagram of one example of a wireless earpiece within a set of wireless earpieces in accordance with an embodiment of the present invention.

FIG. 2 is a block diagram illustrating a device 60 which may be housed within the earpiece housing 12 in accordance with an illustrative embodiment. Where the device 60, such as an earpiece wearable 10, includes more than one wireless earpiece 10 some of the sensors 32 and other components may be housed in one earpiece 10 housing while other components may be housed within the other earpiece housing 12. In addition, sensor data 13 may be received from other devices in operative communication with the device 60.

The device 60 may include one or more LEDs 20 electrically connected to a processor 30. The LEDs 20 may provide relevant information, prompts, alerts, or other indicators to the user. The processor 30 may include multiple processors, digital signal processors, microcontrollers, application specific integrated circuits (ASICs), or other types of integrated circuits. The processor 30 may include an artificial intelligence framework 18. The artificial intelligence framework 18 may be implemented in hardware, software, or combinations thereof to take sensor data, historical data, user settings, and other information to generate contextual information. The artificial intelligence framework 18 may utilize information from the sensors 32 to determine applicable information related to the user, such as physical state, emotional state, location, activity, proximity to other users, activity/actions, well-being, and so forth. The artificial intelligence framework 18 may include any number of machine learning models, convolutional neural networks (CNNs), hidden Markov models (HMMs), natural language processing, deep neural networks (DNNs), or other models of algorithms as may be implemented in hardware and/or software.

The processor 30 may also be electrically connected to one or more sensors 32. Where the device 60 is a wireless earpiece 10, the sensor(s) 32 may include an inertial sensor 74, another inertial sensor 76. Each inertial sensor 74, 76 may include an accelerometer, a gyro sensor or gyrometer, a magnetometer or other type of inertial sensor. The sensor(s) 32 may also include one or more contact sensors 72, one or more bone conduction microphones 71, one or more air conduction microphones 70, one or more chemical sensors 79, a pulse oximeter 78, a temperature sensor 80, or other physiological or biological sensor(s). Further examples of physiological or biological sensors include an alcohol sensor 83, glucose sensor 85, or bilirubin sensor 87. Other examples of physiological or biological sensors may also be included in the device 60. These may include a blood pressure sensor 82, an electroencephalogram (EEG) 84, an Adenosine Triphosphate (ATP) sensor 86, a lactic acid sensor 88, a hemoglobin sensor 90, a hematocrit sensor 92 or other biological or chemical sensors. Other types of sensors may be present based on specific configurations or needs (e.g., radiation sensor, barometer, wind sensor, gas/material sensor, etc.).

A spectrometer 116 is also shown. The spectrometer 116 may be an infrared (IR) through ultraviolet (UV) spectrometer although it is contemplated any number of wavelengths in the infrared, visible, x-ray, or ultraviolet spectrums may be detected. The spectrometer 116 is preferably adapted to measure environmental wavelengths for analysis and recommendations and thus may be located on or at the external facing side of the device.

An image sensor 88 may be present and a depth or time of flight camera 89 may also be present. A gesture control interface 36 may also be operatively connected to or integrated into the processor 30. The gesture control interface 36 may include one or more emitters 82 and one or more detectors 84 for sensing user gestures. The gestures performed may be performed such as through contact with a surface of the earpiece 10 or may be performed near the earpiece 10. The emitters 82 may be of any number of types including infrared LEDs. The device may include a transceiver 35 which may allow for induction transmissions such as through near field magnetic induction. A short-range transceiver 34 using Bluetooth, BLE, UWB, or other means of radio communication may also be present. The short-range transceiver 34 may be used to communicate with other devices including mobile devices. The various sensors 32, the processor 30, and other electronic components may be located on one or more printed circuit boards of the device. One or more speakers 73 may also be operatively connected to the processor 30. A magnetic induction electric conduction electromagnetic (E/M) field transceiver 37 or other type of electromagnetic field receiver may also operatively be connected to the processor 30 to link it to the electromagnetic field of the user. The use of the E/M transceiver 37 allows the device to link electromagnetically into a personal area network or body area network or other devices. It is contemplated sensors associated with other devices including other wearable devices or internet of things (IoT) devices may be used to provide or add to sensor data which may be used to help in establishing context used for making advice.

The artificial intelligence framework 18 may be used to determine context based on the user data or to otherwise apply artificial intelligence. For example, the one or more inertial sensors 74, 76 may be used to determine orientation and movement of a user. The various biometric sensors may be used to detect additional information about a user. Sensor data may be used to determine what a user is doing, who is around the user, an activity the user is engaged in, the mood of the user, stress levels, well-being, the user's heart rate, and other information.

The artificial intelligence framework 18 may also be used not only to determine advice for the user but also to determine a contextually relevant time to deliver the advice to the user. The contextually relevant time is a time which, based on available data and/or relationships between different data sets, is determined to be a time at which the advice is useful or especially useful to the user. For example, the contextually relevant time may be when the user is engaged in a particular activity, has completed a particular activity, is present at a particular location, has left a particular location. The contextually relevant time may be when a user is in a particular mood or exhibiting a particular emotion as may be apparent from physiological sensors. The contextually relevant time may be when the user is with another individual or set of individuals as may be determined from voice analysis, image analysis, or other types of data processing.

The memory 40 is a hardware element, device, or recording media configured to store data or instructions for subsequent retrieval or access later. The memory 40 may represent static or dynamic memory. The memory 40 may include a hard disk, random access memory, cache, removable media drive, mass storage, or configuration suitable as storage for data, instructions, and information. In one embodiment, the memory 40 and the processor 30 may be integrated. The memory 40 may use any type of volatile or non-volatile storage techniques and mediums. The memory 40 may store information related to user input/commands, peripheral actions associated with the commands, communications identifiers, authorizations, as well as the status of a user 106, wireless earpieces 10, mobile device 4, and other peripherals (such as in an IoT network), such as a tablet, smart glasses, a smart watch 844, a smart case for the wireless earpieces 10, a wearable device, and so forth. In one embodiment, the memory 40 may display instructions, programs, drivers, or an operating system for controlling the gesture control interface 36 including one or more LEDs or other light emitting components, speakers, tactile generators (e.g., vibrator), and so forth. The memory 40 may also store thresholds, conditions, signal or processing activity, proximity data, and so forth.

Figure 3:
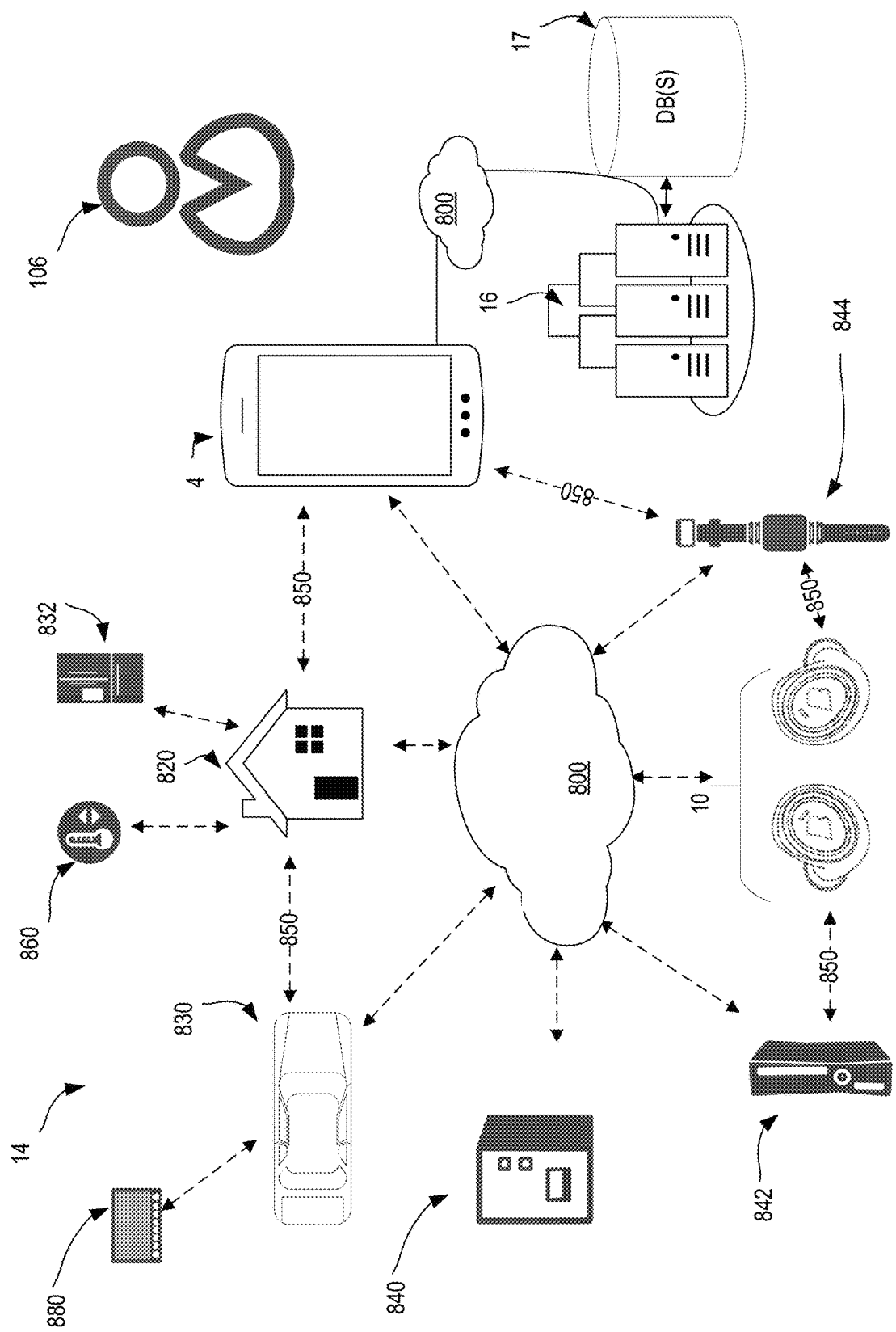
FIG. 3 illustrates a network in an illustrative embodiment of the present invention.

With reference to FIG. 3 a network in an illustrative embodiment is shown. Wireless earpieces 10 may communicate with peripheral devices through network 14, which is shown in FIG. 3 as being an IoT network 14. IoT 14 is a network of physical devices, vehicles 830, home appliances 832 and other items embedded with electronics, software, sensors, actuators and network connectivity which enables these objects to connect and exchange data. Each peripheral device is uniquely identifiable through its embedded computing system but can inter-operate within the existing Internet infrastructure 800. The IoT 14 allows peripheral devices to be sensed, communicated with or controlled remotely across existing network infrastructure 800, creating opportunities for more direct integration of the physical world into computer-based systems, and resulting in improved efficiency, accuracy and economic benefit in addition to reduced human intervention.

Peripheral devices in the IoT 14, can refer to a wide variety of devices such as vending machine 840, gaming system 842, smart watch 844, automobiles 830 with built-in sensors, smart home 820 or mobile device 4. These devices collect useful data with the help of various existing technologies and then autonomously flow the data between other devices.

Wireless earpieces 10, as discussed above, can link and pair with a peripheral device within the IoT 14. The peripheral devices can be a gaming system 842, smart watch 844, mobile device 804, smart home 820, vehicle 830 and a vending machine 840. These items are but a small list of the possible IoT devices. While only a handful of peripheral devices have been shown in the present application, it is fully contemplated most any device may be a peripheral device without departing from the spirit of the invention.

Wireless earpieces 10 can identify and couple with any identifiable peripheral device, either locally through direct communications 850 or through an internet network 800. Once wireless earpieces 10 are paired with the peripheral devices, wireless earpieces 10 can control functionality, communicate and/or receive sensor data from these peripheral devices. Furthermore, wireless earpieces 10 can receive sensor data from other peripheral devices through the IoT 14. This sensor data can be used by the AI framework 18 to provide advice and recommendations to user 106 based upon time, location, activity of user 106, activity going on around the user 106, previous activities of the user 106 (such as purchases), current weather conditions, biometric data of user 106, etc.

As each peripheral device operating within the existing Internet infrastructure 800 is uniquely identifiable through its embedded computing system, wireless earpieces 10 can use this unique identification to identify the peripheral to the user 106. For example, each unique identifier for each peripheral, which identifies the peripheral to another device, can be converted from data into a unique sound which can be sent to user 106. Furthermore, the user 106 can elect to have each identifier correspond to a unique identifying sound of their choice, such as a tone or even a brief snippet of a song.

A user may send voice instructions through the wireless earpieces 10 to smart home 820 to have HVAC system 860 turn the temperature down in smart home 820. In response, HVAC system 860 may advise user 106 the furnace filter needs replacing based upon time expired since last replacement or a sensor within the furnace. AI framework 18 may suggest a good deal on filters, e.g., Filtrete® filters are on sale at Lowes® or AI framework 18 may also suggest a preferred brand e.g., DuPont® and the pricing of nearby locations. The user 106 may also elect not to have the advice reported to them, such as when user 106 wishes not to be interrupted (e.g., during an important phone call or the user simply does not wish to be bothered at the time, etc.). As can be seen in the example above, the suggestion looks less like an advertisement as the user genuinely needs to replace their furnace filter. Thus, AI framework 18 can provide a useful suggestion and or advice to user 106 without having the suggestion appear as advertising.

Further, wireless earpieces 10 may receive a grocery list from smart refrigerator 832 if any grocery shopping needed to be done. Smart refrigerator 832 may have its own identifying sonification tone or may have a corresponding song snippet correlated, such as American Pie by Don McLean or even "Feed Me Seymore" from The Little Shop of Horrors. This grocery list, in data form, may then be sonified for the user into a descriptive listing of the grocery list. For example, a voice may read off the list as needed by the user. The list may be paused at each item and restarted when the item is picked up by user 106. The grocery list may simultaneously be sent to mobile phone 804 for visual reference as well. This application may also be performed with a smart assistant (e.g., Alexa®, Siri®, Google Home® and Cortana®) which speaks directly to the wireless earpieces 802 and allows the user to speak directly through a speaker coupled to the smart assistant to directly speak to the refrigerator 832 or to instruct the smart assistant to speak to or directly control the smart home 820. In this example, user 106 may be notified "orange juice is currently on sale at Target® and the refrigerator is stating you are low on orange juice". Thus, Target would receive an advertisement disguised as advice for a user.

A user 106 can purchase a snack treat out of vending machine 840 through voice commands to wireless earpieces 10. Upon approaching vending machine 840, wireless earpieces 10 may couple with vending machine 840. Wireless earpieces 10 may then inform user 106 the vending machine is stocked with a snack the user likes or has purchased before (all of which may be recorded in the user settings 19, psychological parameters 15, mobile device 4, etc.). The user 106 can instruct vending machine 840 what snack they would like, such as "A7" or by product name. Vending machine 840 would respond in a sonified identifier (e.g., a musical jingle, a voice message, or otherwise) and confirm the purchase with the sonified identifier. When prompted by vending machine 840, wireless earpiece 802 may provide credit/debit information stored within user settings 19 located within memory 40 to vending machine 840. Vending machine 840 may then provide data to the wireless earpieces 10 confirming the successful transaction, which earpieces 802 may sonify as a cash-register "cha-ching". Advice may also be given by AI framework 18 in the following example; if wireless earpieces 10 know the user 106 works out at a certain time, say 1730, and the user is heading to the gym as they pass the vending machine 840, AI framework 18 may suggest a "power bar" or a "sport drink" before user 106 gets to the gym. Thus, a purchase advice may be given without the appearance of an advertisement.

User 106 may also be notified or advised of new release gaming system games, which the user has interest in purchasing. Gaming system 842 may notify wireless earpieces 10 of the availability to purchase a video game user 106 has shown prior interest in. Wireless earpieces 10 may then notify the user 106 through speakers 73 (if the user 106 has allowed notifications to be presented through the speakers). Then, user 106 may instruct their gaming system 842 to begin downloading a game which is currently available. The user may use a voice command to the wireless earpieces 10 to give the instructions over network 800 of IoT 14 and gaming system 842 may begin the ordering and downloading of a game. Gaming system 842 may identify itself with a sound correlation to a brand, such as the auditory marketing identifiers for XBOX® or PlayStation®. Furthermore, the confirmation of the purchase may be audio message and the video game purchased may be identified with a short snippet of a commercial for the game which identifies the game by name. Once again, the AI framework 18 may have identified the video game as "of interest" to the user 106 based upon prior price inquiries of the game, an inquiry into the release date of the game, etc. Gaming system 842 may notify wireless earpieces 10 of the release of the game and AI framework 18 would know user 106 is interested in the game and initiate an audible notice to speakers 73.

Smart watch 844 may couple with wireless earpieces 10 and advise user 106 (s)he has been sitting to long and should get up and move around. Smart watch 844 may also remind the user 106 (s)he has an upcoming run and ask user 106 if (s)he needs to purchase any workout gear. Or smart watch 844 may remind the user 106 they need to purchase stamps, and this would be "a good time to get up move around and pick up some stamps". A user 106 may also send a text via smart watch 844. A user 106 may give an initial instruction to communicate with the smart watch, saying "Smart Watch" and then begin giving instructions to dictate and send a text. Smart watch 844 may identify itself with an identifier converted into sound, or perhaps the user 106 has identified the smart watch 844 with a short snippet of a song or other audio.

Perhaps the user would like to know their biometric readings during their last workout or to have their biometric readings from their last workout stored on database 870 for storage and analysis. Smart watch 844 may send the data to user 106 via wireless earpieces 802 in data form like the pulse oximeter 78 discussed above or a voice may break down the data points for the user 106 in understandable terms. For example, a voice may report "you hit your target heart rate of 150 beats per minute for approximately 17 minutes today burning approximately 375 calories". The user 103 may also simply instruct smart watch 844 through voice or any other type of command to wireless earpiece 802 to have the smart watch 844 perform these functions. Smart watch 844 may also advise the user 106 his current running shoes have over 300 miles currently logged on them and notify the user his(er) the same brand of shoes are currently on sale at a nearby store.

A user may also ask vehicle 830 what the mileage is on vehicle 830 and if vehicle 830 needs servicing. Vehicle 830 may respond with a unique sonified data identifier or the user 106 may have set up a unique music identifier. AI framework 18 may suggest to user 106 the Valvoline® store two blocks down is having a special on oil changes and tire rotation. Or, the AI framework 18 may ask the user 106 if they would like to call their local Firestone® to schedule an appointment to have the oil change performed.

The user may also instruct vehicle 830 to have radio/navigation unit 880 to obtain directions for the user's next trip before the user gets to the vehicle. Vehicle 830 may respond back with a sonified identifier for the Radio, and have a voice confirm directions to the selected destination. All through network 800 of IoT 14 controlled by wireless earpieces 802. AI framework may suggest to user 106 a lunch or meal stop if the trip occurs over a period the user 106 normally eats; suggesting nearby eating locations and narrowing down the eateries to locations catering to the user's diet (e.g., to Keto friendly restaurants).

The wireless earpieces 802 may also utilize edge computing to make operation efficient and seamless. Edge computing is a method of optimizing cloud-computing systems by performing data processing at the edge of the network, near the source of the data. For purposes of the present invention, each peripheral, mobile device 4, vehicle 830, smart home 820, smart watch 844, gaming system 842 and vending machine 840 (peripheral devices) all have a computing system 500. Because each peripheral device has a computing system 500 data processing can be performed at each device, thus reducing the communications bandwidth needed between the peripheral devices and the wireless earpieces 10 by performing analytics and knowledge generation at or near the source of the data; the peripheral devices.

Edge computing pushes applications, data and computing power (services) away from centralized points to the logical extremes of a network 14. Edge computing replicates fragments of information across distributed networks of web servers, which may spread over a vast area. As a technological paradigm, edge computing is also referred to as mesh computing, peer-to-peer computing, autonomic (self-healing) computing, grid computing and by other names implying non-centralized, node-less availability.

Figure 4:
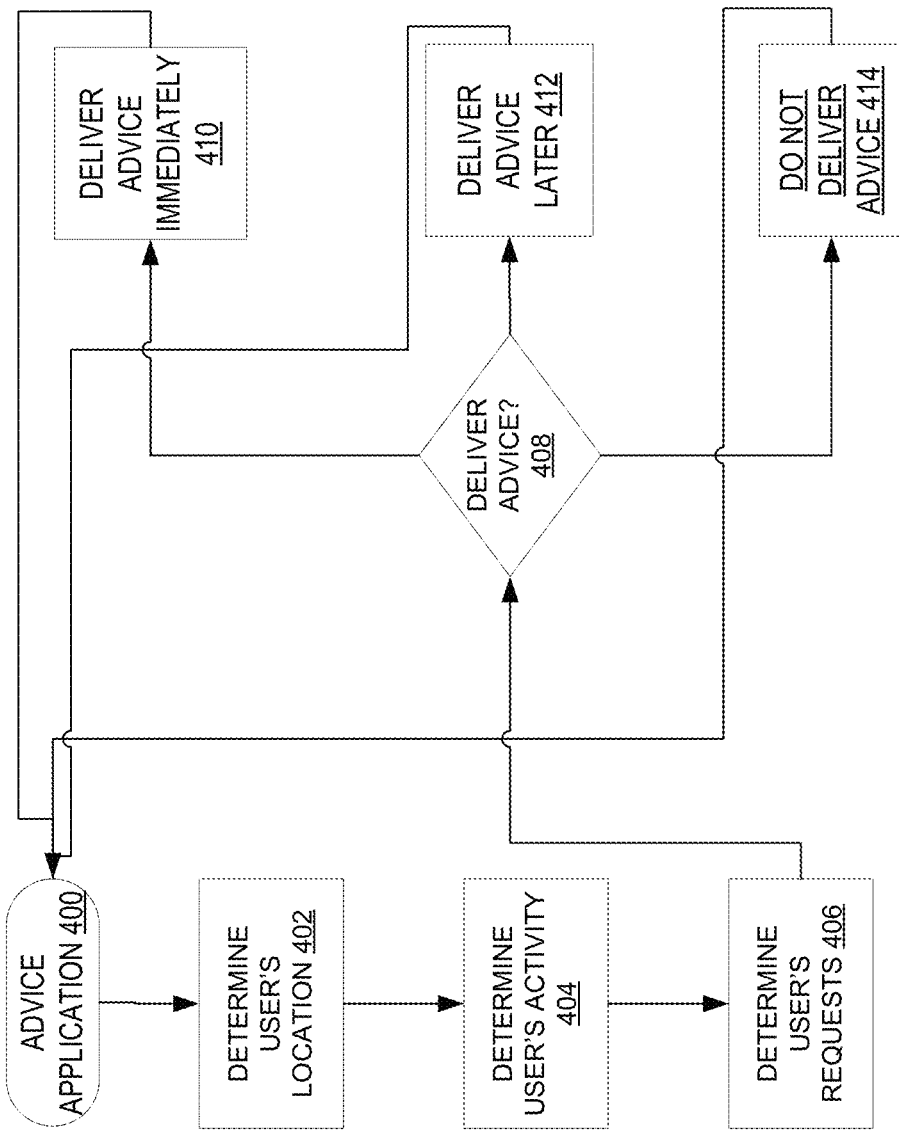
FIG. 4 is a flow chart diagram of an advice application in an embodiment of the present invention.

With reference to FIG. 4, a flow chart diagram of an advice application in an embodiment of the present invention is shown. Advice application 400, may begin by determining the location of user 106 at state 402. The more data AI framework 18 has, the better advice AI framework 18 can provide for the user 106. Thus, AI framework 18 is constantly accepting new data from onboard sensors 32, data from other sensors 13, user settings 19 and psychological parameters 15 to provide user 106 with the best possible advice based upon the user's current surroundings, activities and even history.

Location information can be beneficial to embodiments of the current invention. Through knowledge of where the user 106 is located, advise 11 can be provided through wireless earpieces 10 either based upon user settings 19, psychological parameters 15, data from other sensors 13, IoT network devices or any combination of these inputs.

Where the user 106 is may be determined in various ways. The set of wireless earpieces 10 may utilize a global positioning system receiver 98, wireless triangulation (e.g., cellular, Wi-Fi, Bluetooth, etc.), beacons, a compass and travel indicators (e.g., steps, swimming strokes, pedal strokes, etc.), inertial navigation based on movement (e.g., dead reckoning) utilizing inertial sensors 74 and 76 or other applicable information to determine the location of the user 106.

The set of wireless earpieces 10 may be in operative communication with a mobile device such as a mobile phone 4 or other type of receptor device including a communication link such as a cellular transceiver or Wi-Fi transceiver. For example, the set of wireless earpieces 10 may use a BLE or BLUETOOTH transceiver to communicate with the mobile phone 4 which also has a BLE or BLUETOOTH transceiver as well as a cellular transceiver, a Wi-Fi transceiver, and a GPS receiver or other type of location determining device as may be found in smart phones of various types. The location of the user may then be communicated to the set of wireless earpieces 10. Alternative methods of locating a user or more precise methods of locating a user may also be used.

For example, when the wireless earpieces 10 connect with a smart home 820, then the location of the user 106 may be smart home 820. Similarly, if the wireless earpieces 10 connects with a smart vehicle 830 then the location of the user 106 may be in the smart vehicle 830. It is to be understood for purposes of the illustrative embodiments, the location of the user 106 is not necessarily merely a set of GPS coordinates or other geolocation, but also may include the significance of a location to the user 106 such as smart home 820, work, smart vehicle 830, gym, etc. In the case of a vehicle 830, the location of the vehicle 830 itself may change. In addition, where the set of wireless earpieces 10 include inertial sensors 74 and 76, more specific information regarding a location, position, and orientation of the user 106 may be determined. Other information may be used to further refine a location of the user 106 such as identifying other devices within range of the set of wireless earpieces 10. Thus, in some instances a building where the user 106 is located may be determined, or even a room within a building. Audio processing may also be used to identify sounds or sound sources which may be indicative of location of a user 106 or descriptors of a location of a user 106.

Location information may also be determined in whole or part when the device is a part of a personal area network, a body area network or IoT network 14. Thus, information from other devices within the network 14 may be used to assist in location determination.

At state 404, advice application 400 may determine what activity user 106 was performing.

Further context may be provided which is indicative of what the user 106 is doing. The user 106 may specify what the user 106 is doing. For example, the user may specify what they are doing by responding to a question posed to them through speakers 73 and speaking into air mic 70 or bone mic 71; walking, running, biking, swimming, or otherwise specify their activity. Alternatively, the activity the user 106 is engaged in may be determined based on content. This may include audio processing to identify sounds or sound sources. This may include monitoring orientation or movement with inertial sensor 74 and/or 76. This may include monitoring other devices which the earpieces 10 may connect to such as through Bluetooth, BLE, or otherwise.

Where one or more image sensors 88 are present on the wireless earpieces 10, images may also be acquired and analyzed by processor 30 to provide additional contextual information regarding what the user 106 is doing, the location or environment the user is within, other individuals or objects within the environment, and other contextual information.

It should be noted, the determination of what the user 106 may be doing may take into consideration the form factor for the wireless device 10. For example, where the device is a wearable which is being worn by a user, there may be more use of physiological sensors such as when the device is an earpiece 10, a sensor patch, or other type of device.

At state 406, advice application 400 can determine any requests being made by the user 106. Further context may be provided by the voice commands given through the wireless earpiece 10. For example, the user 106 may be asking questions looking for specific information. This information may be used to further provide context. For example, where the user 106 has asked about the weather or heat index, the wireless earpiece 10 may suggest sunscreens with titanium dioxide because of their effectiveness and suggest snow cone and ice cream shops in the area for cooling down.

A state 408, advice application 400 can decide if it should deliver advice information to user 106, hold the advice information or not give the advice at all. The wireless earpieces 10 can perform an analysis to determine when to deliver the advice. In some instances, it may be preferable to deliver the advice immediately (state 410), in other instances, it may be beneficial to wait to deliver the advice (state 412) and in some instances the advice will not be delivered at all (state 414). The processor using the artificial framework may determine that it is best to wait to deliver the advice until a point in time when the advice may be more useful to the user 106 or to when the user 106 will be in a better position to act on the advice. Thus, the processor is configured to use the artificial intelligence framework to determine a contextually relevant time to deliver the advice to the user which may be immediately, after the completion of a particular event, at the start of a particular event, at a particular location, when physiological sensors indicate a certain condition or otherwise. Thus, the advice may be delivered to the user at the contextually relevant time.

For example, if the user 106 is currently engaged in a phone conversation, the wireless earpieces may wait to deliver the advice until the phone call is over (state 412). Similarly, if the user is engaged in a conversation or in physical activity, the wireless earpieces may wait until such activities have ended before delivering the advice (state 412). The wireless earpieces may wait until the user is at a particular location, with other particular people, experiencing a particular emotional state, or otherwise. Where the wireless earpieces having access to other data through a network additional data may be used to assist in providing context. For example, this may include weather data for the user's location. This may include financial data for the user so that advice to purchase a particular product or service is given at a time when the user has the financial resources to purchase the product or service. This may include data related to emotions of the user such as sports scores that may affect the emotions of a user, or other data that provides context as to when to best deliver the advice.

It is further contemplated the user 106 may control whether advice is given and/or the timing of the advice at state 408. In one mode of operation, advice may be given only when asked for. For example, at the end of the day, the user 106 may reflect upon the day and ask the wireless earpieces 10 for any advice. The wireless earpieces 10 may then provide all the advice collected throughout the day, at state 412, or since the last time advice was requested. In another mode of operation, advice may be shared as soon as it is generated. It is also contemplated the advice may be time, location and activity dependent. For example, if wireless earpieces 10 had advice for user 106 based upon the user's current location, but the user 106 was on the phone at the time and thus wireless earpieces 10 would hold the advice at state 412. However, when the user is off the phone and the user 106 is no longer in the location, then the advice would be considered moot and application 400 would proceed to state 414 and not deliver the advice as the advice is no longer relevant as the user is no longer at the applicable location.

The wireless earpieces 10 may also be configured to provide advice based on emergency, dangerous, or deteriorating circumstances. Valuable pieces of advice may include "you need to drink water to prevent dehydration", "your blood sugar levels are too low, you need to eat a healthy snack", "there have been two shark bites in this area in the last two days", "this area has a high crime rate", "consider riding the bike path nearby instead of on the road", "make sure you have clothes to keep you warm tonight as the low temperature is 38 degrees Fahrenheit", "this section of the river has class 5 rapids", "there is a storm wall approaching 20 miles from here with the potential for tornados", "five accidents have been reported ahead because of black ice", "rattlesnakes have been reported as very active in this area", "children have been observed playing on this road", and so forth. Emergency advice would normally be given immediately at state 410, however, the user 106 may create degrees of emergency within the user settings 19. For example, a warning of rattlesnakes would have greater emergency and the user 106 may prefer for this high priority advice to be allowed to interrupt telephone calls. Whereas, a warning of a high heat index may be lower on the emergency spectrum and thus would be held until a user was available or held for a later time at state 412.

In some instances, instead of delivering information directly to the user 106 at state 410, other actions may be taken. For example, the user 106 may have initiated settings making observation or occurrence of an action or event automatically triggered for information supply or initiation of purchases without additional human interaction.

The wireless earpieces 10 may monitor contextual information associated with a user's ability to hear to make recommendations and provide advice to help the user hear better. For example, the wireless earpiece 10 may include functionality which allows it to serve as an over-the-counter (OTC) wearable hearing device. Thus, for example, the hearable device may provide for amplification of environmental sounds. In more advanced applications, the hearable device may provide for administering hearing tests as disclosed in U.S. patent application Ser. No. 15/674,972, entitled "Earpiece for audiograms", hereby incorporated by reference in its entirety, or for providing tinnitus masking as disclosed in U.S. Patent Application No. 62/474,993, entitled "Wireless earpiece for tinnitus therapy", also hereby incorporated by reference in its entirety. Although such functionality may be very useful and convenient for users, such devices do not necessarily address all the issues which may be addressed through use of conventional hearing aids.

The wireless earpiece(s) 10 may be configured to determine the user may suffer from tinnitus. If the AI framework 18 determines the user 106 may have a hearing problem, AI framework 18 can suggest or advise the user 106 to take a hearing test. If the user elects to do so, the wireless earpiece 10 can run though the frequency(s) at which a user hears a sound without an identifiable source (a tinnitus frequency), and to filter this frequency out of the user's selected audio sources. Thus, the tinnitus frequency may be identified as well as a perceived db SPL of the tinnitus frequency. Subtraction may be provided for incoming audio including onboard music or other stored audio, environmental sounds being sensed and reproduced as a part of an audio transparency mode, as well as anything streamed to the device including phone calls, audio from linked devices including streaming music, audio associated with videos, or other audio.

The wireless earpiece 10 or set of earpieces 10 may include a wireless earpiece housing, a tinnitus diagnosis system, and a therapeutic filtering system. The audio source may include different tones. When the user hears a tone matching his or her perceived tinnitus tone, the user can confirm the tone. After the user confirms the tone, the frequency of the tone is transmitted to the therapeutic filtering system. The tone may be transmitted using a linear continuous-time filter, or another type of filter. The filter may be integrated with logic of the wireless earpieces to limit the bandwidth of the output signal to the band allocated for transmission. The filter may also work with the logic or a transceiver to allow signals within a select range of frequencies to be heard, thereby filtering out the tinnitus frequency. After the filter has removed the tinnitus tone from the user's desired audio source, the audio source may be stored on the earpiece or in another location, so the user can replay it. The filtered audio source may need to be amplified and then transformed into a digitally encoded signal to be stored in memory. The user may also filter new streams of audio without storing those first audio sources. The user can track how often he or she is practicing the tinnitus therapy by downloading software to the earpiece which communicates with an application. According to user presets, each time the user listens to an audio source, the duration of time, type of audio, volume, etc., may be sent to the application or tracked by the user via the application. The application may be located on a different device.

If the wireless earpiece identifies a potential issue such as indicators the tinnitus therapy is not working for the user, the wireless earpiece may generate advice. The advice may be for example, suggesting the user visit an audiologist or suggesting one or more audiologists from a list of audiologists located near the user. The advice may be even more specific to indicate an observed condition for the user to share with the audiologist.

In one embodiment, the wireless device may be a basic tinnitus device. The basic tinnitus device may include a pre-loaded audio file such as an MP3 or MP4 file. Playback of this audio file may simply be looped. The audio file may reside on a processor such as a digital signal processor. Alternatively, the audio file may be stored in another memory such as in onboard storage which may be on the same chip as the digital signal processor or on a different chip. In one configuration, an advice announcement would play upon entry of the device into the ear, or alternatively every x time of insertion. For example, every third time or every fifth time to advise the user of what the next option would be if symptoms of tinnitus are still occurring. The determination of when the device is placed in the ear may occur in various ways such as through use of an inertial sensor, one or more contact sensors, or other sensors. The advice provided may be customized based on the user, the fitting agent who fits the tinnitus device to an ear of a user, the company selling the tinnitus device to the user, or based on other variables such as what to do if the device does not sufficiently solve the problem. According to another aspect, one or more alternative audio outputs may be selected which may include white noise, pink noise, one or more environmental sounds such as babbling brook, gentle rain seashore, or other sounds. This selection may occur via any number of forms of user input including voice input, movement sensing with an inertial sensor, a touch interface, gestural control interface, or otherwise. Data monitoring of usage criteria may be given to a user in multiple ways such as through audio of an earpiece or communicated to another device such as a smart watch or viewed in an app setting on a mobile phone, tablet, or computer. Useful information may be communicated without the perception of the information possibly being potentially sponsored content or advertising. The information presented may be customized to the user based on their preferences, environmental data sensed, or other contextual information.

In another application, the wireless earpiece 10 may be used to make a recommendation as to when to replace sports equipment. For example, as discussed above, the wireless earpiece 10 may be used to make a recommendation as to when to replace running shoes. This recommendation may be performed in any number of different ways. In one embodiment, the distance run with a pair of shoes may be tracked. Onboard inertial sensors 74 and/or 76 may be used to determine distance associated with any run. In addition, the user 106 may use an associated app on mobile device 4 to identify their sports equipment, so miles run may be associated with a set of shoes. For example, if a runner is rotating between two pairs of shoes, the user 106 can set which pair of shoes to use for a run. Alternatively, the pair of shoes may be determined in various other ways such as through image analysis of imagery from the image sensors 88 or other devices in operative communication with the earpieces 10. When the distance exceeds 300-400 miles, or other lifespan for the shoes (such as visual wear and tear), the device may make a recommendation to replace the shoes. In addition, the AI framework 18 may make a recommendation as to what type of shoes to purchase. This may be based on running style as identified through a data analysis of inertial sensor data, body weight of the individual, age, and/or other available information. The recommendation is formulated to take into consideration not merely personal preferences of the user 106 but also results of data analysis to provide true expert advice. It is also contemplated, to better inform the analysis, the wireless earpieces 10 may query the user 106 for additional information or to confirm information. Thus, the wireless earpieces 10 serve as a true advisor to the user.

In this example, the wireless earpieces 10 would determine when the run had ended and provide the advice at the end of the run, as opposed to during the run when a user may find such advice distracting. Alternatively, the advice may be presented when the user 106 enters a store where running shoes are sold and thus may be conducive to receiving the advice. Of course, the advice may be provided at other relevant times as well. In some embodiments, the recommendations may be divided into revenue generating advice and general advice.

In one embodiment, the wireless earpieces 10 may recommend a music or podcast service to the user 106 based on retrieved information. For example, streamed content or the lack of content may be utilized as an indicator to recommend a service, such as Spotify, Soundcloud, or others. A manufacturer, service provider, or company associated with the wireless earpieces 10 may receive a referral fee. The wireless earpieces 10 may also recommend the most popular or all available services without any bias or suggestions for the user to evaluate. Indications of potential services may be periodically provided to the user 106 without the necessity to purchase the service. For example, available services may be mentioned every six months to confirm the user's interest or non-interest.

It should further be understood not every piece of advice need involve a product or service purchase recommendation. Instead, information may also be provided. For example, if the artificial intelligence (AI) platform 18 of the earpiece determines the user is likely to go outside, the earpiece 10 may advise the user 106 to consider wearing sunglasses, if the earpiece 10 has determined it is sunny. Similarly, the earpiece 10 may advise the user 106 to wear sunscreen if the earpiece 10 has determined it is sunny. Thus, the advice may be to use something already existing. Thus, in these examples, the user 106 is advised to use a type of product or even a brand of product which they already have. It is noted this type of recommendation, may assist in building brand loyalty in an acceptable manner. It is to be further understood that information regarding the advice, when it was delivered, and any contextual data associated with the user prior to, at the time of, and/or after the delivery of the advice may be recorded and used by the artificial intelligence framework. This may be used to determine if the advice was of interest, if the advice was followed, the amount of time taken for the user to act on the advice, or other contextual data.

The wireless earpiece may also develop contextual data based on the perceived actions by the user. In some instances, the earpiece may be able to directly determine if the user acted on the advice. For example, if the advice was for the user to perform a particular activity such as to slow down or stop that can be determined from inertial sensors, image data or other data then this information may be used to provide feedback to improve delivery of further advice, better determine the type of advice of interest to the user, better determine the time to deliver advice or otherwise. In addition or alternatively, external data may be used from sponsors of particular advice to provide feedback as to whether the advice was followed or otherwise of interest. The feedback may be in the form of whether a particular product or service was purchased used, or other data.

Figure 5:
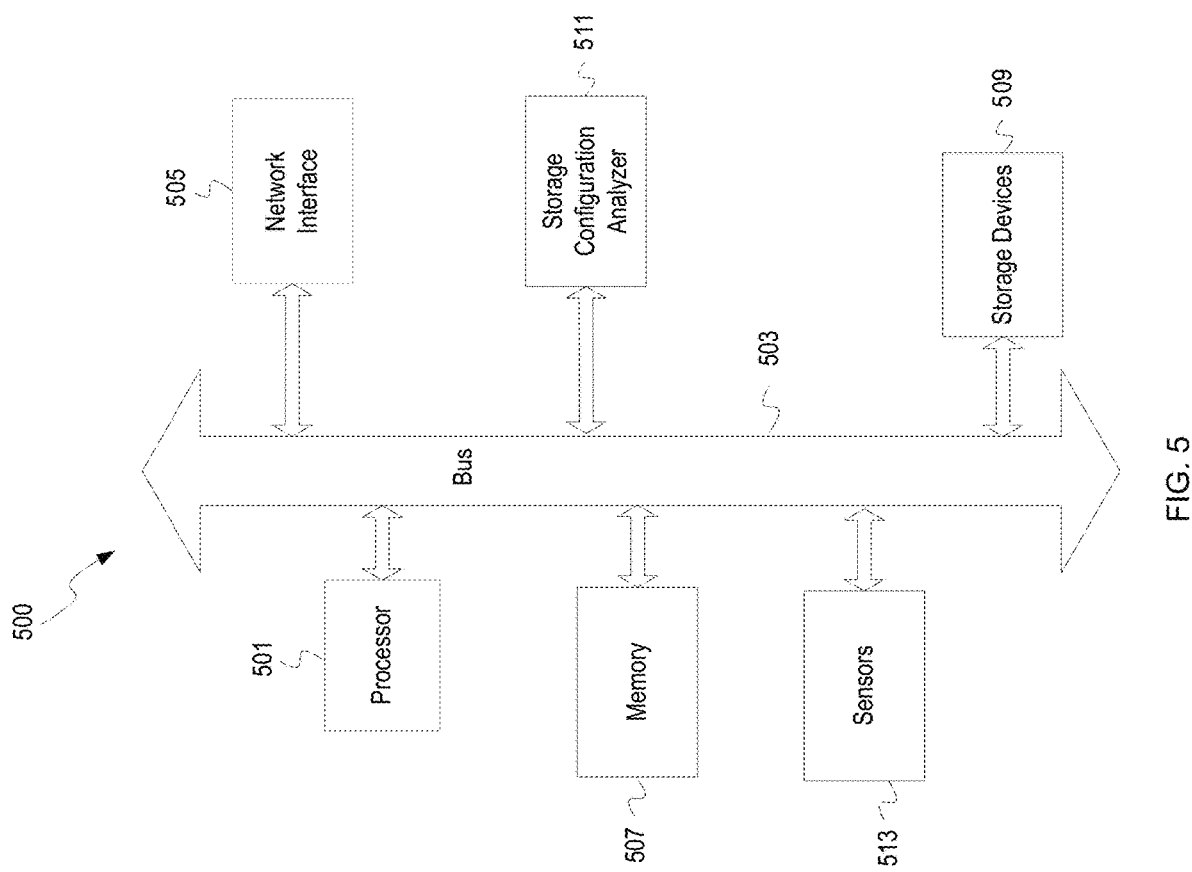
FIG. 5 depicts a computing system in accordance with an illustrative embodiment of the present invention.

FIG. 5 depicts a computing system 500 in accordance with an illustrative embodiment. For example, the computing system 500 may represent a device, such as the wireless device 4 or IoT peripherals (smart watch 844, game console 842, vending machine 840, vehicle 830, radio/navigation unit 880, smart home 820, thermostat 860, refrigerator 832) of FIG. 3. The computing system 500 includes a processor unit 501 (possibly including multiple processors, multiple cores, multiple nodes, and/or implementing multi-threading, etc.). The computing system includes memory 507. The memory 507 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 503, a network interface 506, and a storage device(s) 509 (e.g., optical storage, magnetic storage, etc.).

The system memory 507 embodies functionality to implement all or portions of the embodiments described above. The system memory 507 may include one or more applications or sets of instructions for implementing a peripheral management mode with one or more wireless earpieces 10. In one embodiment, specialized peripheral management software may be stored in the system memory 507 and executed by the processor unit 502. The peripheral management software may be utilized to manage user preferences (e.g., settings, automated processes, etc.), communications, input, and device actions, synchronize devices, or so forth. As noted, the management application or software may be similar or distinct from the application or software utilized by the wireless earpieces 10. Code may be implemented in any of the other devices of the computing system 500. Any one of these functionalities may be partially (or entirely) implemented in hardware and/or on the processing unit 501. For example, the functionality may be implemented with an application specific integrated circuit, in logic implemented in the processing unit 501, in a co-processor on a peripheral device or card, etc. Further, realizations may include fewer or additional components not illustrated in FIG. 5 (e.g., video cards, audio cards, additional network interfaces, peripheral devices, etc.). The processor unit 501, the storage device(s) 509, and the network interface 505 are coupled to the bus 503. Although illustrated as being coupled to the bus 503, the memory 507 may be coupled to the processor unit 501. The computing system 500 may further include any number of sensors 513, such as optical sensors, accelerometers, magnetometers, microphones, gyroscopes, temperature sensors, and so forth for verifying user biometrics, or environmental conditions, such as motion, light, or other events may be associated with the wireless earpieces or their environment.

The illustrative embodiments may be utilized to control and manage advice (e.g., audio, video, data, etc.) played, displayed, or communicated by one or more peripherals as managed through the wireless earpieces 10. For example, music may be streamed from the wireless earpieces 10 to one or more wireless speakers whether directly or through an intermediary device (e.g., smart phone, repeater, etc.). For example, the wireless earpieces 10 may control a smart phone synchronized with a Bluetooth speaker. In one embodiment, the wireless earpieces 10 may automatically connect to a nearest peripheral. For example, the wireless earpieces and the peripheral may have been previously paired. In another embodiment, the wireless earpieces may connect to a peripheral based on user input, feedback, or instructions, such as a directional gesture, voice command, head motion, or so forth. The wireless earpieces may be linked, connected, or paired (or disconnected, unpaired) in real-time based on user input. For example, the wireless earpieces may switch between a first link with a first peripheral to a second link with a second peripheral.

Therefore, various methods, systems, and apparatus have been shown and described. Although specific embodiments are set forth herein, the present invention is not to be limited to these embodiments as numerous options, variations, and alternatives are contemplated.

What is claimed is:

1. An earpiece comprising:
an earpiece housing;
at least one speaker;
a plurality of sensors disposed within the earpiece housing;
a processor disposed within the earpiece housing and operatively connected to the plurality of sensors and the at least one speaker;
wherein the processor is configured to use an artificial intelligence framework to evaluate sensor input from the plurality of sensors to generate advice to a user based at least in part on context of location of the user and activity of the user;
wherein the processor is configured to use the artificial intelligence framework to determine the activity of the user using sensor input from the plurality of sensors;
wherein the processor is configured to use the artificial intelligence framework to determine a contextually relevant time to deliver the advice to the user based at least in part on the location of the user and the activity of the user;
wherein the processor is configured to delay the delivery of the advice to the user until the contextually relevant time.

2. The earpiece of claim 1, wherein the advice is in a form of information.

3. The earpiece of claim 1, wherein the advice is in a form of a product or service recommendation.

4. The earpiece of claim 3, wherein the product or service recommendation for a product or service of a sponsor.

5. The earpiece of claim 1, wherein the wherein the contextually relevant time to deliver the advice to the user is further based on a determination of a mood of a user.

6. The earpiece of claim 1, wherein the earpiece provides for tinnitus relief.

7. The earpiece of claim 6, wherein the advice to the user is associated with tinnitus.

8. The earpiece of claim 7, wherein the earpiece further includes a memory and wherein an audio file for treating tinnitus is stored on the memory.

9. A device comprising:
a housing;
at least one speaker;
a plurality of sensors disposed within the housing; and
a processor disposed within the housing and operatively connected to the plurality of sensors and the at least one speaker;
wherein the processor is configured to use an artificial intelligence framework to evaluate sensor input from the plurality of sensors to generate advice to the user, to use the artificial intelligence framework to determine a contextually relevant time to deliver the advice to the user, and to delay the delivery of the advice to the user until the contextually relevant time;
wherein the contextually relevant time is determined by the artificial intelligence framework by a location of the user and content of speech of the user.

10. The device of claim 9, further comprising a transceiver operatively connected to the processor for operative communication with a network of one or more additional devices.

11. The device of claim 10, wherein each of the one or more additional devices include one or more sensors and wherein the one or more additional devices are each configured to communicate data from the one or more sensors to the processor of the device.

12. The device of claim 11, wherein the device is an earpiece and wherein the housing is an earpiece housing.

13. The device of claim 12, wherein the network is an IoT network.

14. A method of providing advice using a device, the method comprising:
monitoring a plurality of sensors using the device; and
using an artificial intelligence platform of the device to generate advice to a user of the device based on contextual understanding at least partially determined using data from the plurality of sensors;
using the artificial intelligence platform of the device to determine a contextually relevant time to deliver the advice to the user, the contextually relevant time at least partially determined using additional data from the plurality of sensors and wherein the additional data is used by the artificial intelligence platform to determine mood of the user;
delivering the advice to the user through the device after a delay and at the contextually relevant time.

15. The method of claim 14, wherein the advice is in a form of information.

16. The method of claim 14, wherein the advice is in a form of a product or service recommendation.

17. The method of claim 16, wherein the product or service recommendation is for a product or service of a sponsor.

18. The method of claim 16, further comprising the step of determining a location of the user.

19. The method of claim 18, further comprising the step of determining the user's activity.

20. The method of claim 19, further comprising the step of determining whether the user has made any requests and wherein the advice is based at least in part on context of a location of the user, an activity of the user, and any requests made by the user.

* * * * *